(12) United States Patent
Folger et al.

(10) Patent No.: US 9,616,134 B2
(45) Date of Patent: *Apr. 11, 2017

(54) LIQUID PREPARATION COMPRISING PIMOBENDAN

(71) Applicants: Martin Folger, Ingelheim am Rhein (DE); Stefan Lehner, Wiesbaden (DE)

(72) Inventors: Martin Folger, Ingelheim am Rhein (DE); Stefan Lehner, Wiesbaden (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 154 days.

This patent is subject to a terminal disclaimer.

(21) Appl. No.: 14/261,838

(22) Filed: Apr. 25, 2014

(65) Prior Publication Data

US 2014/0235648 A1 Aug. 21, 2014

Related U.S. Application Data

(63) Continuation of application No. 11/935,129, filed on Nov. 5, 2007.

(30) Foreign Application Priority Data

Nov. 7, 2006 (EP) .................... 06123567

(51) Int. Cl.
| | | |
|---|---|---|
| *A61K 31/33* | (2006.01) | |
| *A61K 47/40* | (2006.01) | |
| *A61K 9/00* | (2006.01) | |
| *A61K 9/08* | (2006.01) | |
| *A61K 31/501* | (2006.01) | |
| *A61K 47/48* | (2006.01) | |
| *B82Y 5/00* | (2011.01) | |

(52) U.S. Cl.
CPC ............ *A61K 47/40* (2013.01); *A61K 9/0019* (2013.01); *A61K 9/08* (2013.01); *A61K 31/501* (2013.01); *A61K 47/48969* (2013.01); *B82Y 5/00* (2013.01)

(58) Field of Classification Search
CPC .............. A61K 47/40; A61K 47/48969; A61K 31/501; A61K 9/08; A61K 9/0019; B82Y 5/00
USPC .................................................. 514/252.06
See application file for complete search history.

(56) References Cited

U.S. PATENT DOCUMENTS

| | | |
|---|---|---|
| 3,574,859 A | 4/1971 | Kosti |
| 3,822,349 A | 7/1974 | Kosti |
| 3,832,460 A | 8/1974 | Kosti |
| 3,839,522 A | 10/1974 | Kosti |
| 3,950,333 A | 4/1976 | Durant et al. |
| 4,128,658 A | 12/1978 | Price et al. |
| 4,256,743 A | 3/1981 | Goldhaber |
| 4,283,400 A | 8/1981 | von Bittera et al. |
| 4,283,408 A | 8/1981 | Hirata et al. |
| 4,293,557 A | 10/1981 | Shibata et al. |
| 4,361,563 A | 11/1982 | Austel et al. |
| 4,375,547 A | 3/1983 | Pioch |
| 4,386,099 A | 5/1983 | Cereda et al. |
| 4,427,648 A | 1/1984 | Brickl et al. |
| 4,569,837 A | 2/1986 | Suzuki et al. |
| 4,585,790 A | 4/1986 | Padfield et al. |
| 4,596,705 A | 6/1986 | Schepky et al. |
| 4,654,342 A | 3/1987 | Slater |
| 4,704,284 A | 11/1987 | Beatty et al. |
| 4,732,915 A | 3/1988 | Ayer et al. |
| 4,851,226 A | 7/1989 | Julian et al. |
| 4,868,182 A | 9/1989 | Dage |
| 4,906,628 A | 3/1990 | Coates |
| 4,933,182 A | 6/1990 | Higashi et al. |
| 4,954,501 A | 9/1990 | Herter et al. |
| 4,973,469 A | 11/1990 | Mulligan et al. |
| 5,024,998 A | 6/1991 | Bodor |
| 5,151,420 A | 9/1992 | Backstrom et al. |
| 5,188,836 A | 2/1993 | Muhammad et al. |
| 5,364,646 A | 11/1994 | Gruber et al. |
| 5,569,657 A | 10/1996 | Nore et al. |
| 6,407,079 B1 | 6/2002 | Muller et al. |
| 6,476,078 B1 | 11/2002 | Jerussi et al. |
| 6,713,487 B2 | 3/2004 | Yu et al. |
| 7,262,165 B2 | 8/2007 | Lindenblatt et al. |
| 8,409,612 B1 | 4/2013 | Criere et al. |
| 8,980,894 B2 | 3/2015 | Daemmgen et al. |
| 2003/0162835 A1 | 8/2003 | Staniforth et al. |
| 2003/0190343 A1 | 10/2003 | Thombre et al. |
| 2003/0212114 A1 | 11/2003 | Sato |
| 2004/0037869 A1 | 2/2004 | Cleverly et al. |
| 2004/0152664 A1 | 8/2004 | Chang et al. |
| 2004/0157887 A1 | 8/2004 | Whittle et al. |

(Continued)

FOREIGN PATENT DOCUMENTS

| | | |
|---|---|---|
| CA | 950833 A1 | 7/1974 |
| CA | 1222697 A1 | 6/1987 |

(Continued)

OTHER PUBLICATIONS

Kitzen et al (Cardiovascular drug Reviews, 1988, 6(4), 265-291).*
Kitzen (Cardiovascular drug Reviews, 1988, 6(4), 265-291, cited in the previous Office Action).*
Pagel et al., "Comparison of the effects of levosimendn, pimobendan, and milrinone on canine left ventricular-arterial coupling and mechanical efficiency". Basic Respiratory Cardiology, vol. 91, 1996, pp. 296-307.
Ettinger et al., "Therapeutic Considerations in Medicine and Disease". Textbook of Veterinary Internal Medicine, Diseases of the Dog and Cat, Sixth Edition, vol. I, 2004, pp. 530-531.

(Continued)

*Primary Examiner* — Jason Sims
*Assistant Examiner* — Ibrahim D Bori
(74) *Attorney, Agent, or Firm* — Michael P. Morris; Wendy M. Gombert (57) ABSTRACT

A liquid preparation includes an etherified cyclodextrin derivative and a substituted benzimidazol, where the etherified cyclodextrin derivative is one of alpha-, beta, and gamma-cyclodextrin ether.

12 Claims, 2 Drawing Sheets

(56) References Cited

U.S. PATENT DOCUMENTS

| | | |
|---|---|---|
| 2005/0095293 A1 | 5/2005 | Brauns et al. |
| 2005/0203097 A1 | 9/2005 | Folger et al. |
| 2005/0239692 A1 | 10/2005 | Lindenblatt et al. |
| 2007/0112010 A1 | 5/2007 | Kleeman et al. |
| 2008/0207629 A1 | 8/2008 | Folger et al. |
| 2009/0082282 A1 | 3/2009 | Daemmgen et al. |
| 2010/0035889 A1 | 2/2010 | Daemmgen et al. |
| 2010/0183718 A1 | 7/2010 | Ovaert et al. |
| 2010/0273807 A1 | 10/2010 | Kleeman et al. |
| 2011/0251208 A1 | 10/2011 | Daemmgen et al. |
| 2011/0318420 A1 | 12/2011 | Hu et al. |
| 2012/0148640 A1 | 6/2012 | Folger et al. |
| 2012/0308662 A1 | 12/2012 | Konishi et al. |
| 2013/0115301 A1 | 5/2013 | Bele et al. |
| 2013/0203690 A1 | 8/2013 | Daemmgen et al. |
| 2014/0155338 A1 | 6/2014 | Daemmgen et al. |
| 2015/0025082 A1 | 1/2015 | Aven et al. |
| 2015/0150820 A1 | 6/2015 | Laczay |

FOREIGN PATENT DOCUMENTS

| | | |
|---|---|---|
| CA | 2034569 A1 | 7/1991 |
| CA | 1336498 C | 8/1995 |
| CN | 1662250 A | 8/2005 |
| CN | 1702243 A | 11/2005 |
| DE | 3728244 A1 | 3/1989 |
| DE | 4001623 A1 | 7/1991 |
| EP | 0241179 A1 | 10/1987 |
| EP | 0256566 A1 | 2/1988 |
| EP | 0268146 A1 | 5/1988 |
| EP | 0306846 A2 | 3/1989 |
| EP | 0330052 A2 | 8/1989 |
| EP | 0335545 A2 | 10/1989 |
| EP | 0349657 A1 | 1/1990 |
| EP | 439030 A2 | 7/1991 |
| EP | 1247456 A2 | 10/2002 |
| EP | 1260215 A1 | 11/2002 |
| EP | 1579862 A1 | 9/2005 |
| EP | 1903039 A1 | 3/2008 |
| EP | 1920785 A1 | 5/2008 |
| FR | 2350105 A1 | 12/1977 |
| GB | 1045031 A | 10/1966 |
| GB | 2228004 A | 8/1990 |
| JP | 61500788 A | 4/1986 |
| JP | H029825 A | 1/1990 |
| JP | H0489428 A | 3/1992 |
| JP | H0570612 A | 3/1993 |
| JP | H11228302 A | 8/1999 |
| JP | 2005281283 A | 10/2005 |
| JP | 2007191419 A | 8/2007 |
| JP | 2008504308 A | 2/2008 |
| JP | 2011157390 A | 8/2011 |
| JP | 2012533595 A | 12/2012 |
| JP | 2013006798 A | 1/2013 |
| JP | 2013503113 A | 1/2013 |
| WO | 8502767 A1 | 7/1985 |
| WO | 8904178 A1 | 5/1989 |
| WO | 9531963 A1 | 11/1995 |
| WO | 0069414 A2 | 11/2000 |
| WO | 0135925 A1 | 5/2001 |
| WO | 0164190 A1 | 9/2001 |
| WO | 0197861 A2 | 12/2001 |
| WO | 0245693 A1 | 6/2002 |
| WO | 0249646 A1 | 6/2002 |
| WO | 03012030 A2 | 2/2003 |
| WO | 03074032 A1 | 9/2003 |
| WO | 03075895 A1 | 9/2003 |
| WO | 03097067 A1 | 11/2003 |
| WO | 03099194 A2 | 12/2003 |
| WO | 2004000317 A1 | 12/2003 |
| WO | 2004000344 A1 | 12/2003 |
| WO | 2004016252 A1 | 2/2004 |
| WO | 2004033444 A1 | 4/2004 |
| WO | 2004050657 A2 | 6/2004 |
| WO | 2004058726 A2 | 7/2004 |
| WO | 2004060353 A1 | 7/2004 |
| WO | 2004089418 A1 | 10/2004 |
| WO | 2005035505 A2 | 4/2005 |
| WO | 2005084647 A1 | 9/2005 |
| WO | 2005092343 A1 | 10/2005 |
| WO | 2005107756 A1 | 11/2005 |
| WO | 2006000229 A2 | 1/2006 |
| WO | 2006022562 A1 | 3/2006 |
| WO | 2006060122 A2 | 6/2006 |
| WO | 2006060127 A2 | 6/2006 |
| WO | 2007038796 A1 | 4/2007 |
| WO | 2007054514 A2 | 5/2007 |
| WO | 2008055871 A1 | 5/2008 |
| WO | 2010060874 A1 | 6/2010 |
| WO | 2011009818 A1 | 1/2011 |
| WO | 2013135852 A1 | 9/2013 |
| WO | 2015082389 A1 | 6/2015 |

OTHER PUBLICATIONS

Piel et al., "Development of a parenteral and of an oral formulation of albendazole with cyclodextrins". S.T.P. Pharma Sciences, vol. 9, No. 3, 1999, pp. 257-260.

Rackley, Charles E., "Diseases of the Heart and Pericardium"., The Merck Manual, Chapter 25, 16th Edition, 1992, pp. 446-459.

Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.

Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.

Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.

Rodriguez, Damon B., "Treatment of Feline Hypertrophic Cardiomyopathy". Compendium, vol. 24, No. 6, Jun. 2002, pp. 470-476.

Roland et al., "The Use of Pimobendan in Feline Heart Failure Secondary to Spontaneous Heart Disease". The 18th Annual ECVIM Congress, Abstract, Belgium, Sep. 2008, 1 page.

Rudnic et al., "Oral Solid Dosage Forms". Remington: The Science and Practice of Pharmacy, 20th Edition, Lippincott Williams & Wilkins, Baltimore, Maryland, Chapter 45, 2000, pp. 858-870.

Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.

Sabbah et al., "Effects of long-term monotherapy with enalapril, metoprolol, and digoxin on the progression of left ventricular dysfuntion and dilation in dogs with reduced ejection fraction". Circulation, vol. 89, 1994, pp. 2852-2859.

Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.

Shiga et al., "b-Blocker Therapy Combined with Low-Dose Pimobendan in Patients with Idiopathic Dilated Cardiomyopathy and Chronic Obstructive Pulmonary Disease: Report on Two Cases". Cardiovascular Drugs and Therapy, vol. 16, 2002, pp. 259-263.

Sisson et al., "Myocardial Diseases of Dogs". Textbook of Canine and Feline Cardiology: Principles and Clinical Practice, Second Edition, Chapter 27, Saunders, 1999, pp. 581-619.

Sisson, David, "Lecture Notes: Cardiology", The District of Columbia Academy of Veterinary Medicine, May 2001, pp. 1-18.

(56) References Cited

OTHER PUBLICATIONS

Summerfield et al., "Efficacy of Pimobendan in the Prevention of Congestive Heart Failure or Sudden Death in Doberman Pinschers with Preclinical Dilated Cardiomyopathy (The PROTECT Study)". Journal of Veterinary Internal Medicine, vol. 26, 2012, pp. 1337-1349.

Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.

The American Heritage Dictionary, homogeneous, Last Accessed Feb. 10, 2011, 1 page, http://www.xreferplus.com/entry/hmdictenglang/homogeneous.

Tomanek et al., "Growth of the Coronary Vasculature in Hypertrophy: Mechanisms and Model Dependence". Cellular and Molecular Biology Research, vol. 40, No. 2, 1994, pp. 129-136.

Van Meel et al., "Pimobendan Increases Survival of Cardiomyopathic Hamsters". Journal of Cardiovascular Pharmacology, vol. 13, 1989, pp. 508-509.

Villar et al., "Ibuprofen, Aspirin and Acetaminophen Toxicosis and Treatment in Dogs and Cats". Veterinary and Human Toxicology, vol. 40, No. 3, Jun. 1998, pp. 156-162.

Wikipedia, the Free Encyclopedia, "Milrinone". [Accessed at: http://en.wikipedia.org/wiki/Milrinone on Mar. 10, 2014].

Wikipedia, the Free Encyclopedia, "Pimobendan". [Accessed at: http://en.wikipedia.org/wiki/Pimobenan on Mar. 10, 2014].

Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.

Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.

Fujino et al., "Differential Effects of d- and I-Pimobendan on Cardia Myofilament Calcium Sensitivity". The Journal of Pharmacology and Experimental Therapeutics, vol. 247, No. 2, 1988, pp. 519-523.

Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.

Groban, Leanne, "Diastolic Dysfunction in the Older Heart". Journal of Cardiothoracic and Vascular Anesthesia, vol. 19, No. 2, Apr. 2005, pp. 228-236.

Gwathmey et al., "Abnormal Intracellular Calcium Handling in Myocardium From Patients With End-Stage Heart Failure". Circulation Research, vol. 61, No. 1, 1987, pp. 70-76.

Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, pp. 225-233.

Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.

Häggstrom et al., "Effect of Pimobendan or Benazepril Hydrochloride on Survival Times in Dogs with Congestive Heart Failure Caused by Naturally Occurring Myxomatous Mitral Valve Disease: The QUEST Study". Journal of Veterinary Internal Medicine, vol. 22, 2008, pp. 1124-1135.

Häggstrom et al., "Longitudinal Analysis of Quality of Life, Clinical, Radiographic, Echocardiographic, and Laboratory Variables in Dogs with Myxomatous Mitral Valve Disease Rexceiving Pimobendan or Benazepril: The Quest Study". Journal of Veterinary Internal Medicine, 2013, pp. 1-11.

Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.

Häggström et al., "New insights into degenerative mitral valve disease in dogs". Veterinary Clinics Small Animal Practice, vol. 34, 2004, pp. 1209-1226.

International Search Report and Written Opinion for PCT/EP2007/061879 mailed on Mar. 18, 2008.

Iwasaki et al., "Pimobendan Inhibits the Production of Proinflammatory Cytokines and Gene Expression of Inducible Nitric Oxide Synthase in a Murine Model of Viral Myocarditis". Journal of the American College of Cardiology, vol. 33, No. 5, 1999, pp. 1400-1407.

Jain et al., "Effects of Milrinone on Left Ventricular Remodeling After Acute Myocardial Infarction". Circulation, vol. 84, No. 2, Aug. 1991, pp. 798-804.

Kashem et al., "CardioClasp: A New Passive Device to Reshape Cardiac Enlargement". ASAIO Journal, vol. 48, No. 3, 2002, pp. 253-259.

Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, pp. 1311-1351.

Kato, Kazuzo, "Clinical Efficacy and Safety of Pimobendan in Treatment of Heart Failure-Experience in Japan". Cardiology, vol. 88, Supp. 2, 1997, pp. 28-36.

Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.

Kittleson et al., "The Acute Hemodynamic Effects of Milrinone in Dogs With Severe Idiopathic Myocardial Failure". Journal of Veterinary Medicine, vol. 1, 1987, pp. 121-127.

Koob et al., "Acute Effects of Furosemide on Blood Electrolytes and Hemodynamics in Dogs". Angiology, 1978, pp. 463-472.

Kubo et al, "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.

Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.

Lachman et al., "The Theory and Practice of Industrial Pharmacy"., 3rd Edition, Lea & Febiger, Philadelphia, 1986, pp. 58-60.

Lai et al., "Real Time and Noninvasive Monitoring of Dry Powder Blend Homogeneity". AIChE Journal, vol. 47, No. 11, Nov. 2001, pp. 2618-2622.

Lamb et al., "Assessment of the value of the vertebral heart scale in the radiographic diagnosis of cardia disease in dogs". Veterinary Record, vol. 146, 200, pp. 687-690.

Lewis et al., "Near-Infrared Chemical Imaging for Product and Process Understanding". in Process Analytical Technology, Second Edition, John Wiley & Sons, Ltd., United Kingdom, 2010, pp. 272-276.

Lewis, Alan B., "Clinical Profile and Outcome of Restrictive Cardiomyopathy in Children". American Heart Journal, vol. 123, No. 6, 1992, pp. 1589-1593.

Lip et al., "ABC of heart failure: Aetiology". British Medical Journal, vol. 320, Jan. 2000, pp. 104-107.

Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.

Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.

Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, pp. 249-261.

Lombard, Christophe W., "Therapy of Congestive Heart Failure in Dogs with Pimobendan". Proceedings of the 18th Annual Veterinary Medical Forum, American College of Veterinary Internatl Medicine, Seattle, WA, 2000, pp. 107-1093.

(56) References Cited

OTHER PUBLICATIONS

Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.
Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.
Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art. 17, Sep. 2002, pp. 1-15.
Malik et al., "Permethrin Spot-On Intoxication of Cats: Literature review and survey of veterinary practitioners in Australia". Journal of Feline Medicine and Surgery, vol. 12, 2010, pp. 5-14.
Mamoru et al., "Effects of Long-term, Very-low-dose Pimobendan for Patients with Diastolic Heart Failure". Journal of Cardial Failure, vol. 12, No. 8, Oct. 2006, p. S171.
Matsumori et al., "Pharmacology letters: Accelerated Communication: Pimobendan inhibits the activation of transcription factor NF-kB A mechanism which explains its inhibition of cytokine production and inducible nitric oxide synthase". Life Sciences, vol. 67, 2000, pp. 2513-2519.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.
Medline, homogeneous, Merriam-Webster, Last Accessed Feb. 10, 2011, 1 page, http://www.merriam-webster.com/medlineplus/homogeneous.
Menard et al., "Physico-Chemical Aspects of the Complexation of Some Drugs with Cyclodextrins". Drug Development and Industrial Pharmacy, vol. 16, No. 1, 1990, pp. 91-113.
Merriam-Webster, homogeneous, Last Accessed Feb. 10, 2011, 2 pages, http://www.merriam-webster.com/dictionary/homogeneous.
Monnet et al., "Idiopathic Dilated Cardiomyopathy in Dogs: Survival and Prognostic Indicators". 1995, Journal of Veterinary Internal Medicine, vol. 9, No. 1, pp. 12-17.
Ng, Tien M.H., "Levosimendan, a New Calcium-Sensitizing Inotrope for Heart Failure". Pharmacotherapy, vol. 24, No. 10, 2004, pp. 1366-1384.
O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.
Ohte et al., "The Cardia Effects of Pimobendan (But Not Amrinone) Are Preserved at Rest and During Exercise in Conscious Dogs with Pacing-Induced Heart Failure". The Journal of Pharmacology and Experimental Therapeutics, vol. 282, No. 1, 1997, pp. 23-31.
Okazaki et al., "A genetic linkage map of the Syrian hamster and localization of cariomyopathy locus on chromosome 9qa2.1-b1 using RLGS spot-mapping". Nature Genetics, vol. 13, May 1996, pp. 87-90.
Packer et al., "Effect of Oral Milrinone on Mortality in Severe Chronic Heart Failure." The New England Journal of Medicine, vol. 325, No. 21, Nov. 1991, pp. 1468-1475.
Pagel et al., "Influence of levosimendan, pimobendan, and milrinone on the regional distribution of cardiac output in anaesthetized dogs". British Journal of Pharmacology, vol. 119, 1996, pp. 609-615.
Permanetter et al., "Acute Effects of Intravenous UD-CG 115 BS (Pimobendan) on the Cardiovascular System and Left Ventricular Pump Function". Journal of Cardiovascular Pharmacology, vol. 14, Supp. 2, 1989, pp. S36-S40.

Baur et al., "Cardiac remodelling and myocardial contractility in patients with congestive heart failure treated with furosemide and enalapril". Basic Research in Cardiology, vol. 86, Supp. 1, 1991, pp. 157-163.
Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.
Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, 1992, pp. 1311-1351.
Thiel et al., "Content uniformity of microdose tablets (dosage 1 µg-10 mg) produced by fluid bed granulation of interactive mixtures". Journal of Pharmacy and Pharmacology, vol. 38, 1986, pp. 335-343.
Petit et al., "Vetmedin® 1.25 mg, Vetmedin® 5 mg, Chewable tablets, Inodilator (pimobendan) tablet for dogs". Dictionary of Veterinary Drugs and Animal Health Products Marketed in France, 16th Edition, Les Editions du Point Vétérinaire, 2011, pp. 1658-1661.
"Vetmedin®—1,25 mg appetizing tablets for dogs Veterinary use". Summary of Product Characteristics, SCS Boehringer Ingelheim Comm. V, Mar. 25, 2009, pp. 1-4.
"Rimadyl F 50 mg". Summary of Product Characteristics, Zoetis France, May 15, 2013, pp. 1-4.
Hemati et al., "Fluidized bed coating and granulation: influence of process-related variables and physicochemical properties on the growth kinetics". Powder Technology, vol. 13, 2002, pp. 18-34.
Lamb et al., "Assessment of the value of the vertebral heart scale in the radiographic diagnosis of cardia disease in dogs". Veterinary Record, vol. 146, 2000, pp. 687-690.
Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, Jul./Aug. 2006, pp. 249-261.
Brewster et al., "Cyclodextrins as pharmaceutical solubilizers". Advanced Drug Delivery Reviews, vol. 59, No. 7, 2007, pp. 645-666.
Vidal et al., "Making sense of antisense". European Journal of Cancer, vol. 41, 2005, pp. 2812-2818.
Pirollo et al., "Targeted Delivery of Small Interfering RNA: Approaching Effective Cancer Therapies". Cancer Research, vol. 68, No. 5, Mar. 2008, pp. 1247-1250.
Phillips et al., "The challenge of gene therapy and DNA delivery". Journal of Pharmacy and Pharmacology, vol. 53, 2001, pp. 1169-1174.
Abstract in English for JPH0489428, 1992.
Ash et al., "Receptor Mediating Some Actions of Histamine". British Journal of Pharmacology and Chemotherapy, vol. 27, No. 2, Aug. 1996, pp. 427-439.
Black et al., "Definition and Antagonism of Histamine H2-receptors". Nature, vol. 236, Apr. 1972, pp. 385-390.
Dews et al., "The Antihistamine Substance 2786 R.P." British Journal of Pharmacology, vol. 1, 1946, pp. 278-286.
Loew, Earl R., "Gastric Secretion in Dogs Treated with Histamine Antagonist, Thymoxyethyldiethylamine". Experimental Biology and Medicine, vol. 48, No. 1, Oct. 1941, pp. 65-68.
Lantz et al., "Stability of nizatidine in extemporaneous oral liquid preparations". American Journal of Hospital Pharmacy, vol. 47, No. 12, Dec. 1990, pp. 2716-2719.
Nakamoto et al., "The role of ascorbic acid deficiency in human gingivitis—a new hypothesis". Journal of Theoretical Biology, vol. 108, No. 2, May 1984, pp. 163-171.
Pernsteiner et al., "Effect of Topical Application of Phenylephrine Hydrochloride on Hyperplastic Gingivitis". Journal of Periodontology, vol. 48, No. 8, Aug. 1977, pp. 473-477.
Trendelenburg, U. "The Action of Histamine and 5-Hydroxytryptamine on Isolated Mammalian Atria". The Journal of Pharmacology and Experimental Therapeutics, vol. 130, No. 4, Dec. 1960, pp. 450-460.

(56) References Cited

OTHER PUBLICATIONS

"905 Uniformity of Dosage Units". 2011 The United States Pharmacopeial Convention, Stage 6 Harmonization, Dec. 1, 2011, pp. 1-3.
"Cardiovascular system". MIMS, IVS Annual, Chapter 5, 2003, p. 104.
"Citric Acid". The Merck Index, an Encyclopedia of Chemicals, Drugs, and Biologicals, 13th Edition, Merck Research Laboratories Division of Merck & Co., Inc., Whitehouse Station, NJ, Index 2350, 2001, pp. 405-406.
"Guidance for Industry, Container Closure Systems for Packaging Human Drugs and Biologics: Chemistry, Manufacturing, and Controils Documentation". U.S. Department of Health and Human Services Food and Drug Administration, May 1999, pp. 1-56.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, an Encyclopedia of Chemicals, Drugs, and Biologicals, 13th Edition, Merck Research Laboratories Division of Merck & Co., Inc., Whitehouse Station, NJ, Index 7515, 2001, p. 1332.
Abstract in English for CN1702243A, 2005.
Abstract in English for DE3728244,1989.
Abstract in English for EP0306846, 1989.
Abstract in English for EP0330052, 1989.
Abstract in English for JP2005281283, 2005.
Abstract in English of JPH0570612, 1993.
Abstract in English of JPH11228302, 1999.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure". Journal of Cardiovascular Pharmacology, vol. 23, No. 2, 1994, pp. 268-274.
Atkins et al., "Guidelines for the Diagnosis and Treatment of Canine Chronic Valvular Heart Disease". Journal of Veterinary Internal Medicine, vol. 23, No. 6, 2009, pp. 1-9.
Banker et al., "Uniformity of Dosage Units". Modern Pharmaceutics, Fourth Edition, Revised and Expanded, Marcel Dekker, Inc., New York, NY, 2006, p. 498.
Bassani et al., "Enhanced Water-Solubility of Albendazole by Hydroxy-Propyl-β-Cyclodextrin Complexation". Journal of Inclusion Phenomena and Molecular Recognition in Chemistry, vol. 25, No. 1-3, Mar. 1996, pp. 149-152.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Baur et al., "Cardiac remodelling and myocardial contractility in patients with congestive heart failure treated with furosemide and enalapril". Basic Research in Cardiology, vol. 86, Supp. 1, pp. 157-163.
Beers, et al., Merck Manual of Diagnosis and Therapy, 17th Edition, Chapter 203, Section 16, Merck Research Laboratories, Whitehouse Station, NJ, USA, 1999, pp. 1688-1692.
Berny et al., "Review: Animal Poisoning in Europe. Part 2: Companion Animals". The Veterinary Journal, vol. 193, 2010, pp. 255-259.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Borgarelli et al., "Canine Idiopathic Dilated Cardiomyopathy. Part II: Pathophysiology and therapy". The Veterinary Journal, vol. 162, 2001, pp. 182-195.
Bozzone, Scott, "Solid Oral Dosage Forms Powder Blending" and "Solid Oral Dosage Forms, Blend Uniformity: Principles and Examples". Pfizer, IKEV Meeting, May 31, 2001, pp. 1-66.
Buchanan et al. "Vertebral scale system to measure canine heart size in radiographs". Journal of the American Veterinary Medical Association, vol. 206, No. 2, Jan. 1995, pp. 194-199.
Burlage et al., "Other Pharmaceutical Adjuncts"., Physical and Technical Pharmacy, the Blakiston Division: The McGraw-Hill Book Company, Inc., New York, 1963, pp. 653-662.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cambridge Dictionary, homogeneous, Last Accessed Feb. 10, 2011, 1 page, http://dictionary.cambridge.org/dictionary/british/homogeneous.
Chambers 21st Century Dictionary, homogeneous, Last Accessed Feb. 10, 2011, 1 page, http://www.xreferplus.com/entry/chambdict/homogeneous.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Choy et al., "Scaling of myocardial mass to flow and morphometry of coronary arteries". Journal of Applied Physiology, vol. 104, 2008, pp. 1281-1286.
Cohn et al., "Cardiac Remodeling-Concepts and Clinical Implications: A Consensus Paper From an International Forum on Cardiac Remodeling". Journal of the American College of Cardiology, vol. 35, No. 3, 2000, pp. 569-582.
Collins English Dictionary, homogeneous, Last Accessed Feb. 10, 2011, 1 page, http://xreferplus.com/entry/hcengdict/homogeneous.
Conlon, P.D., "Nonsteroidal Drugs Used in the Treatment of Inflammation". Veterinary Clinics of North America: Small Animal Practice, vol. 18, No. 6, Nov. 1988, pp. 1115-1131.
Cowley et al, "Treatment of severe heart failure: quantity or quality of life? A trial of enoximone"., British Heart Journal, vol. 72, 1994, pp. 226-230.
Côté et al., "Congestive Heart Failure". Feline Cardiology, Ch. 19, Wiley-Blackwell, ISBN 978-0-8138-1242-7, 2011, p. 259.
Deneke et al., "Medikamentöse Therapie der Herzinsuffizienz". Herzschr Elektrophys, vol. 15, Suppl. 1, 2004, pp. 1/74-1/80.
Dictionary of Veterinary Drugs and Animal Health Products Marketed in France, 12th Edition, 2003, 3 pages.
El-Hagrasy et al., "A Process Analytical Technology Approach to Near-Infrared Process Control of Pharmaceutical Power Blending: Part II: Qualitative Near-Infrared Models for Prediction of Blend Homogeneity". Journal of Pharmaceutical Sciences, vol. 95, No. 2, Feb. 2006, pp. 407-421.
El-Hagrasy et al., "Near-Infrared Spectroscopy and Imaging for the Monitoring of Powder Blend Homogeneity". Journal of Pharmaceutical Sciences, vol. 90, No. 9, Sep. 2001,. pp. 1298-1307.
Elliott, P., "Diagnosis and management of dilated cardiomyopathy". Heart, vol. 83, 2000, pp. 106-112.
Endoh, Masao, "New Aspects of the Treatment of Myocardial Failure from a Pharmacological Standpoint". Journal of Clinical and Experimental Medicine, vol. 187, No. 10, 1998, pp. 827-831.
Erhardt, L., "An Emerging Role for Calcium Sensitisation in the Treatment of Heart Failure". Expert Opinion on Investigational Drugs, vol. 14, No. 6, 2005, pp. 659-670.
Ettinger et al., "Effects of enalapril maleate on survival of dogs with naturally acquired heart failure". Journal of the American Veterinary Medical Association, vol. 213, No. 11, 1998, pp. 1573-1577.
Fitton et al., "Pimobendan. A Review of its Pharmacology and Therapeutic Potential in Congestive Heart Failure". Drugs and Aging, vol. 4, No. 5, 1994, pp. 417-441.
Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.

(56) References Cited

OTHER PUBLICATIONS

Fox, Philip R., "Hypertrophic Cardiomyopathy. Clinical and Pathologic Correlates". Journal of Veterinary Cardiology, vol. 5, No. 2, Nov. 2003, pp. 39-45.
Stuber et al., "The Pharmaceutical and Biological Availability of Commercial Preparations of Furosemide". Arzneimittel-Forschung, vol. 32, No. 6, 1982, pp. 693-697.
Lezcano et al., "Complexation of Several Benzimidazole-Type Fungicides with Alpha and Beta-Cyclodextrins". Journal of Agricultural and Food Chemistry, vol. 50, 2002, pp. 108-112.
Redenti et al., "Drug/Cyclodextrin/Hydroxy Acid Multicomponent Systems. Properties and Pharmaceutical Applications". Journal of Pharmaceutical Sciences, vol. 89, 2000, pp. 1-8.

* cited by examiner

Figure 1

P111 Cyclodextrin Solubility Results

| Reference FD4063 | Kleptose (%w/v) | Initial pH | pH of P111 Solution | Saturated Solubility (mg/ml) |
|---|---|---|---|---|
| 113A | 10 | 2.74 | 3.00 | 0.65 |
| 113D | 20 | 2.78 | 3.24 | 1.59 |
| 113G | 25 | 2.83 | 3.07 | 2.68 |
| 118E | 30 | 2.76 | 3.30 | 3.82 |
| 113N | 40 | 2.99 | 3.48 | 6.30 |
| 113B | 10 | 4.94 | 4.92 | 0.10 |
| 113E | 20 | 5.03 | 4.96 | 0.41 |
| 113H | 25 | 5.05 | 4.99 | 0.96 |
| 118F | 30 | 5.09 | 5.10 | 0.93 |
| 118H | 40 | 5.26 | 5.29 | 4.88 |
| 113C | 10 | 7.10 | 7.08 | 0.15 |
| 113F | 20 | 7.11 | 7.09 | 0.70 |
| 118D | 25 | 7.14 | 7.13 | 1.21 |
| 118G | 30 | 7.14 | 7.14 | 2.41 |
| 134B | 35 | 7.18 | 7.17 | 5.68 |
| 113Q | 40 | 7.20 | 7.19 | 9.94 |

| Concentration of HPβCD (%w/v) | Batch of HPβCD | Pimobendan Content (mg/ml) | | Mean Pimobendan Content (mg/ml) |
|---|---|---|---|---|
| 20 | E0032 | 0.514 | 0.544 | 0.57 |
| | E0033 | 0.559 | 0.510 | |
| | E0035 | 0.773 | 0.524 | |
| 21 | E0032 | 0.617 | 0.947 | 0.67 |
| | E0033 | 0.630 | 0.566 | |
| | E0035 | 0.570 | 0.692 | |
| 22 | E0032 | 0.616 | 0.618 | 0.73 |
| | E0033 | 0.642 | 1.039 | |
| | E0035 | 0.779 | 0.656 | |
| 23 | E0032 | 0.728 | 0.771 | 1.00 |
| | E0033 | 0.710 | 1.100 | |
| | E0035 | 1.206 | 1.501 | |
| 24 | E0032 | 1.451 | 1.388 | 1.23 |
| | E0033 | 1.099 | 1.383 | |
| | E0035 | 1.000 | 1.061 | |
| 25 | E0032 | 1.654 | 1.641 | 1.37 |
| | E0033 | 1.095 | 1.027 | |
| | E0035 | ND | 1.422 | |

ND – No Pimobendan peak detected, result not used in mean determination.

Figure 4

| Batch of HPβCD | Pimobendan Content (mg/ml) | | Mean Pimobendan Content (mg/ml) |
|---|---|---|---|
| E0032 | 0.697 | 0.676 | 0.71 |
| E0033 | 0.723 | 0.707 | |
| E0035 | 0.716 | 0.728 | |

Figure 5

| Sample | Assay (mg/ml) | Impurity V (%) | Other Impurities |
|---|---|---|---|
| Autoclaved | 0.74 | 0.08 | Not detected |
| Not Autoclaved | 0.74 | Not detected | Not detected |

LIQUID PREPARATION COMPRISING PIMOBENDAN

RELATED APPLICATIONS

This application claims priority to European Application No. EP 06123567.7, filed Nov. 7, 2006, the teachings and content of which are hereby incorporated by reference herein.

FIELD OF INVENTION

The invention relates to the field of medicine. In particular, the invention relates to novel liquid preparation comprising a substituted benzimidazol, preferably pimobendan as pharmaceutically active compound.

BACKGROUND OF THE INVENTION

Pimobendan is a well-known compound for the treatment of congestive heart failure (CHF) originating for example from dilated cardiomyopathy (DCM) or decompensated endocardiosis (DCE) in animals, especially dogs (WO 2005/092343). Pimobendan is also approved as a drug product for cardiovascular treatment of humans.

Pimobendan (4,5-dihydro-6-[2-(4-methoxyphenyl)-1H-benzimidazol-5-yl]-5-methyl-3(2H)-pyridazinone) is disclosed in EP B-008 391, herein incorporated by reference in its entirety, and having the formula:

As already was described in EP A-439 030 and WO 2005/08467, pimobendan drug substance is insoluble in water, 1 g substance is soluble in more than 10000 ml. At pH 7 the solubility of pimobendan is about 0.1 mg per 100 ml.

The substance is administered by the oral route twice daily. Yet no liquid preparation comprising pimobendan is available. In order to achieve an immediate onset of action for all the innovative indications mentioned above, an injectable solution for parenteral administration by the i.v. and/or s.c. route is obligatory. An aqueous formulation is required to administer a drug product by the i.v./s.c. route to either humans or animals, formulations with a non-aqueous solvent are neither acceptable nor state of the art due to the risk of severe tolerance problems.

Solubility in aqueous solutions is depending on the pH. The solubility of pimobendan is significantly higher at pH 1 to 3, however, the chemical stability in solution is reduced so that a stable solution with a reasonable shelf-life cannot be achieved. In addition, the local tolerance of such a formulation is very poor. This is due to the fact that the target dose would require a drug concentration in solution which can only be achieved by a pH of about pH3 and lower. The required concentration in solution exceeds the solubility of pimobendan in water by a factor of about 250, a factor of 1 to 1000 might be the maximum required increase.

Certain etherified beta-cyclodextrin derivatives are known to improve solubility of sparingly soluble drugs (WO85/02767). However, in WO85/02767 only the use of etherified beta-cyclodextrin derivatives up to a concentration of 10% is described. A molar ratio of drug to etherified beta-cyclodextrin derivative of 1:6 to 4:1 was thought. The solubility of flubendazol within the above given ratio was only increased by a factor 30. However, those formulations are not suitable for the preparation of liquid preparations comprising pimobendan, or any other substituted benzimidazol in therapeutically effective amounts of up to 5 mg/ml, preferably of 0.5 to 3 mg/ml, even more preferably of 0.5 to 1.5 mg/ml. As mentioned above, at least pimobendan formulation comprising up to 1.5 mg/ml needs an increase in solubility at pH 7 by a factor of about 1000 to 1500.

The objective underlying the present invention was to provide liquid preparations comprising a substituted benzimidazol, preferably pimobendan as pharmaceutically active compound.

The objective underlying the present invention was to provide a pharmaceutically acceptable solution comprising a substituted benzimidazol, preferably pimobendan as pharmaceutically active compound.

Another objective underlying the present invention was to provide injectable solutions comprising a substituted benzimidazol, preferably pimobendan as pharmaceutically active compound.

DESCRIPTION OF THE INVENTION

DETAILED DESCRIPTION OF THE INVENTION

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

Figure 1:
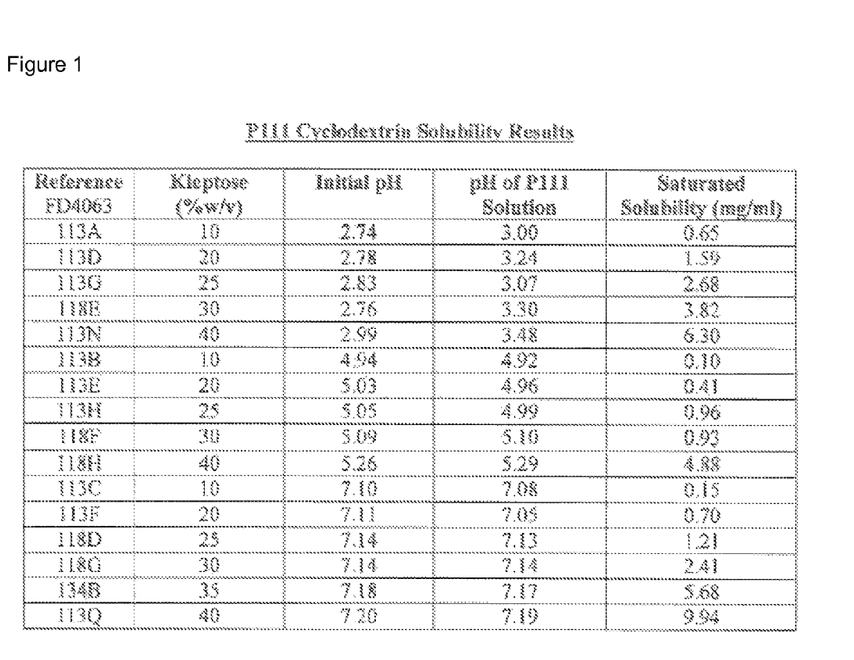
FIGS. 1 and 2 show the saturated solubility of pimobendan, a substituted benzimidazol in an aqueous solution comprising various concentrations of the etherified cyclodextrin derivative hydroxypropyl-beta-cyclodextrin (HPβCD) at pH 3, 5, and 7.

The present invention is based on the unexpected observation that a non-linear relationship exists between the rise in concentration of hydroxypropyl-beta-cyclodextrin (HPβCD), an etherified cyclodextrin derivative, and the increase in solubility of pimobendan a structurally member of a substituted benzimidazol at a pH of about 5 or 7. Solutions containing a target concentration for pimobendan of about 0.5 to 1.5 mg/ml could be obtained by the use of HPβCD concentration of more than 15%, preferably of about 20% (w/v) to up to 70% (w/v) of the final formulation. FIG. 1 teaches, that based on such a non-linear relationship, a HPβCD concentration of more than 20 (w/v) caused in a significant increased solubility of pimobendan, which is used in an exemplarily manner for a substituted benzimidazol. In general, by "(w/v)" as used herein is meant weight of substance per volume of the final preparation/formulation.

In addition, it was an unexpected observation that the solubility enhancement achieved by HPβCD did not decrease at an increasing pH. Solubility of pimobendan at low pH values was in principle higher than at higher pH values. This effect was already known from WO 2005/08467. This also was found for solutions comprising the etherified cyclodextrin derivative HPβCD (See FIG. 1). However, this effect surprisingly is reversed at pH 7.0. The solubility of pimobendan at pH 5 in the presence of HPβCD was significantly reduced as compared to pH 3. Contrary, at pH 7 the solubility of pimobendan in the presence of HPβCD is significantly higher than that pH 5. The relationship between increasing HPβCD concentrations (by mass) and increase in saturated solubility of pimobendan was linear at pH 3, but non-linear at pH 7 (see FIG. 1). The higher the concentration of HPβCD the higher the solubility of pimobendan. This non-linear effects allows an increase of solubility of more than factor 1000, which is needed for the preparation of liquid preparation of pimobendan, or any other substituted benzimidazol comprising therapeutically effective amounts of those active ingredients.

Thus according to one aspect, the present invention relates to a liquid preparation comprising an etherified cyclodextrin derivative and a substituted benzimidazol, wherein the etherified cyclodextrin derivative is selected from the group consisting of: alpha-, beta, and gamma-cyclodextrin ether.

The term "liquid preparation" as used herein, simply means that the majority of the preparation is present in liquid form. The term "liquid preparation" as used herein, includes any form of an aqueous solution as well as any kind of suspension. If the liquid preparation is obtained in the form of a suspension, it is a dispersed system. By a "dispersed system" is meant, in general terms, a systems consisting of two or more phases in which one type of form (dispersed phase) is finely divided in the other type of form (dispersion agent). By a "suspension" is meant, according to the invention, a mixture of solid particles in a liquid. Preferably, the liquid preparation according to the invention is an aqueous solution, more preferably a non-alcoholic aqueous solution. Even more preferably, those liquid preparations are aqueous solutions that are suitable as injectable solutions for i.v. and/or s.c. application in animals. The term "aqueous solution" as used herein, simply means that the majority of the preparation is present in a dissolved form. The term non-alcoholic aqueous solutions as used herein means that preparation is present in a dissolved form but do not include alcoholic or other organic solvents.

Thus according to a further aspect, the present invention relates an aqueous solution comprising an etherified cyclodextrin derivative and a substituted benzimidazol, wherein the etherified cyclodextrin derivative is selected from the group consisting of: alpha-, beta, and gamma-cyclodextrin ether. Preferably, those aqueous solutions are injectable solutions for i.v. and/or s.c. application in animals, or can be can be used for the preparation of injectable solutions for i.v. and/or s.c. application in animals.

The term etherified cyclodextrin derivatives as used herein includes but is not limited to alpha-, beta- or gamma-cyclodextrins. Preferably the etherified cyclodextrin derivatives as used herein means etherified beta-cyclodextrins, more preferably of the formula:

(beta-CD)-OR     (formula I), in which the residues R are hydroxyalkyl groups and part of the residues R may optionally be alkyl groups. A partially etherified beta-cyclodextrin of formula I is preferably used in which the residues R are hydroxyethyl, hydroxypropyl or dihydroxypropyl groups, Optionally part of the residues R may for instance be methyl or -ethyl groups; the use of partially-methylated beta-cyclodextrin ethers with 7 to 14 methyl groups in the beta-cyclodextrin molecule as they are known from German Offenlegungsschrift 31 18 218 do not come under the present invention. Partial ethers of beta-cyclodextrin comprising only alkyl groups (methyl, ethyl) may be suitable in accordance with the invention if they have a low degree of substitution (as defined below) of 0.05 to 0.2.

Even more preferably, the etherified cyclodextrin derivative as used herein is hydroxyethyl-beta-cyclodextrin, hydroxypropyl-beta-cyclodextrin, dihydroxypropyl-beta-cyclodextrin. Most preferably, the etherified cyclodextrin derivative as used herein is hydroxypropyl-beta-cyclodextrin (HPβCD), for example as described in the European Pharmacopoeia (5$^{th}$ Edition 2005, European Directorate for the Quality of Medicines (EDQM), European Pharmacopoeia, 226 avenue de Colmar, F-67029 Strasbourg, France, http://www.pheur.org). Hydroxypropyl-beta-cyclodextrin (HPβCD) of pharmaceutical grade is marketed for example under the Trademark Kleptose® HP and can be ordered from Roquette, France.

Beta-cyclodextrin is a compound with ring structure consisting of 7 anhydro glucose units; it is also referred to as cycloheptaamylose. Each of the 7 glucose rings contains in 2-, 3-, and 6-position three hydroxy groups which may be etherified. In the partially etherified β-cyclodextrin derivatives used according to the invention only part of these hydroxy groups is etherified with hydroxyalkyl groups and optionally further with alkyl groups. When etherifying with hydroxy alkyl groups which can be carried out by reaction with the corresponding alkylene oxides, the degree of substitution is stated as molar substitution (MS), viz. in mole alkylene oxide per anhydroglucose unit, compare U.S. Pat. No. 3,459,731, column 4. In the hydroxyalkyl ethers of beta-cyclodextrin used in accordance with the invention the molar substitution is between 0.05 and 10, preferably between 0.2 and 2. Particularly preferred is a molar substitution of about 0.40 to about 1.50. The etherification with alkyl groups may be stated directly as degree of-substitution (DS) per glucose unit which as stated above—is 3 for complete substitution. Partially etherified beta-cyclodextrins are used within the invention which comprise besides hydroxyalkyl groups also alkyl groups, especially a methyl or ethyl groups, up to a degree of substitution of 0.05 to 2.0, preferably 0.2 to 1.5. Most preferably the degree of substitution with alkylgroups is between about 0.5 and about 1.2.

Thus, according to a further aspect, the present invention relates to liquid preparations as described above, comprising an etherified cyclodextrin derivative and a substituted benzimidazol, wherein the etherified cyclodextrin derivative is etherified beta-cyclodextrin. Preferably, that etherified beta-cyclodextrin is hydroxyethyl-beta-cyclodextrin, hydroxypropyl-beta-cyclodextrin, or dihydroxypropyl-beta-cyclodextrin. Even more preferably, that etherified beta-cyclodextrin is hydroxypropyl-beta-cyclodextrin (HPβCD), for example as described in the European Pharmacopoeia ($5^{th}$ Edition 2005, European Directorate for the Quality of Medicines (EDQM), European Pharmacopoeia, 226 avenue de Colmar, F-67029 Strasbourg, France, http://www.pheur.org). Most preferably, that etherified beta-cyclodextrin is Kleptose® HP (Roquette, France).

The term "substituted benzamidazol" as used herein means, but is not limited to thiabendazol, fuberidazol, oxibendazol, parbendazol, cambendazol, mebendazol, fenbendazol, flubendazol, albendazol, oxfendazol, nocodazol, astemisol and pimobendan, pharmaceutical acceptable salts, derivatives, metabolites or pro-drugs thereof. Preferably, the term substituted benzimidazol as used herein means pimobendan, or any pharmaceutical acceptable salts, derivatives, metabolites or pro-drugs thereof. Pimobendan as such is described supra.

Thus, according to a further aspect, the present invention relates to liquid preparations as described above, comprising an etherified cyclodextrin derivative and a substituted benzimidazol, wherein:
a) the etherified cyclodextrin derivative is etherified beta-cyclodextrin, preferably, hydroxyethyl-beta-cyclodextrin, hydroxypropyl-beta-cyclodextrin, or dihydroxypropyl-beta-cyclodextrin, even more preferably hydroxypropyl-beta-cyclodextrin (HPβCD), and most preferably, Kleptose® HP (Roquette, France); and
b) the substituted benzamidazol is thiabendazol, fuberidazol, oxibendazol, parbendazol, cambendazol, mebendazol, fenbendazol, flubendazol, albendazol, oxfendazol, nocodazol, astemisol or pimobendan, pharmaceutical acceptable salts, derivatives, metabolites or pro-drugs thereof, preferably pimobendan as described supra or any pharmaceutical acceptable salt, derivative, metabolite or pro-drug thereof.

The amount of etherified cyclodextrin that is needed for the liquid preparation depends on the pH of the final liquid preparation, the substituted benzimidazol and the portion that is used. However, it was surprisingly found, that the use of about 15-70% (w/v) of etherified cyclodextrin derivative, preferably HPβCD in the final preparation is appropriate to dissolve an therapeutically effective amount of any of the substituted benzimidazol described above. In particular, it is shown, that the use of about 15-70% (w/v) of etherified cyclodextrin derivatives as described above, preferably of HPβCD in the final preparation is appropriate to dissolve an therapeutically effective amount pimobendan. Thus, according to a further aspect, any of the final liquid preparation as described herein, comprises about 15 to 70% (w/v) etherified cyclodextrin derivative, preferably HPβCD. Preferably the portion of etherified cyclodextrin derivative, preferably of HPβCD; of the final liquid preparation is 20-50% (w/v), even preferably 20-40%, even more preferably 20-30% (w/v), even more preferably 22-28%, even more preferably 23-27% (w/v), even more preferably 24-26% (w/v), for example the portion of the final preparation is 15, 16, 17, 18, 19, 20, 21, 22, 23, 24, 25, 26, 27, 28, 29, 30, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70% (w/v) or any fraction thereof.

The portion of the substituted benzimidazol of the liquid preparation as described herein is as a rule between 0.005 and 0.15% (w/v), preferably between 0.01 and 0.15% (w/w), further preferred between 0.05 and 0.15% (w/w), and even further preferred between 0.075 and 0.10% (w/w). Consequently, the portion is, for example, 0.001, 0.002, 0.003 . . . 0.008, 0.009, etc.; 0.01, 0.02, 0.03, 0.04, 0.05, . . . 0.08 0.09 etc.; 0.10, 0.11, 0.12 . . . 0.14, 0.15% (w/v). Preferably, the substituted benzimidazol is anyone of those described herein, preferably pimobendan.

Thus according to further aspect, the present invention relates to a liquid preparation comprising an etherified cyclodextrin derivative, and a substituted benzimidazol as described above, preferably HPβCD and pimobendan, wherein that liquid preparation comprises:
a) about 15 to 70% (w/v), preferably 20-50% (w/v), even preferably 20-40%, even more preferably 20-30% (w/v), even more preferably 22-28%, even more preferably 23-27% (w/v), most preferably 24-26% (w/v) of such etherified cyclodextrin derivative, preferably of HPβCD; and
b) between 0.005 and 0.15% (w/v), preferably between 0.01 and 0.15% (w/w), further preferred between 0.05 and 0.15% (w/w), and even further preferred between 0.075 and 0.1% (w/w) of a substituted benzimidazol as described herein, preferably of pimobendan.

The general therapeutic effective target dose, in particular for the treatment of acute CHF, but also for any other therapeutic use as described herein is about 0.05 to 0.5 mg pimobendan per kg body weight of the animal, preferably about 0.1 to 0.3 mg pimobendan per kg body weight of the animal, even more preferably about 0.15 mg pimobendan per kg body weight of the animal. The target concentration of pimobendan in the drug product should be set to 0.75 mg/ml allowing the administration of safe and even injection volumes. E.g. a dog with a weight of 10 kg would receive exactly a dose of 2 ml containing 1.5 mg of pimobendan. Thus according to a further aspect, the present invention relates to a liquid preparation, preferably an aqueous solutions for injection, comprising an etherified cyclodextrin derivative as described above, preferably HPβCD and 0.75 mg/ml (0.075% (w/v)) pimobendan. More preferably, the portion of etherified cyclodextrin derivative in that liquid preparation comprises about 15 to 70% (w/v), preferably 20-50% (w/v), even preferably 20-40% (w/v), even more preferably 20-30% (w/v), even more preferably 22-28% (w/v), even more preferably 23-27% (w/v), most preferably 24-26% (w/v) of such etherified cyclodextrin derivative. Most preferred is a liquid preparation, preferably an aqueous solutions for injection, that comprises 0.75 mg/ml (0.075% (w/v)) pimobendan and about 15 to 70% (w/v), preferably 20-50% (w/v), even preferably 20-40% (w/v), even more preferably 20-30% (w/v), even more preferably 22-28% (w/v), even more preferably 23-27% (w/v), most preferably 24-26% (w/v) HPβCD of the final formulation.

The liquid preparations are tolerable to the addition of buffers, antioxidants such as sodium edetate, isotonic agents such as sodium chloride, and are suitable as single-use injectable solutions for i.v. and/or s.c. application in animals, especially dogs. Preservatives can be added, too. Thus, according to a further aspect, the present invention relates to any of the above mentioned liquid preparations, preferably to aqueous solutions for injection, that comprise an etherified cyclodextrin derivative as described herein, preferably HPβCD, and a substituted benzimidazol as described herein, preferably pimobendan, wherein such preparation further comprises pharmaceutical acceptable excipients, and/or salts.

Purely by way of example, the excipients in a standard liquid preparation, in particular in a solution for injection according to the present invention might be meglumin, macrogol, poloxamer 188, parabens and glycin. The formulations according to the invention may contain complexing agents as other ingredients. By complexing agents are meant within the scope of the present invention molecules which are capable of entering into complex bonds. Preferably, these compounds should have the effect of complexing cations, most preferably metal cations. The formulations according to the invention preferably contain edetic acid (EDTA) or one of the known salts thereof, e.g. sodium EDTA or disodium EDTA dihydrate (sodium edetate), as complexing agent. Preferably, sodium edetate is used, optionally in the form of its hydrates, more preferably in the form of its dihydrate. If complexing agents are used within the formulations according to the invention, their content is preferably in the range from 1 to 20 mg per 10 ml, more preferably in the range from 2 to 10 mg per 10 ml of the formulation according to the invention. Preferably, the formulations according to the invention contain a complexing agent in an amount of about 5 mg per 10 ml of the formulation according to the invention. Of course, other excipients known to the skilled man may also be used.

Thus, according to a further aspect, the present invention relates to any of the above mentioned liquid preparations, preferably to aqueous solutions for injection, that comprise an etherified cyclodextrin derivative as described herein, preferably HPβCD, and a substituted benzimidazol as described herein, preferably pimobendan, wherein such preparation further contains one or more suitable preservative(s), preferably selected from the group consisting of meglumin, macrogol, parabens and EDTA.

In the case of the salts these are, for example, inorganic salts such as chloride, sulfate, phosphate, diphosphate, bromide and/or nitrate salts. Furthermore, the powders according to the invention may also contain organic salts such as malate, maleate, fumarate, tartrate, succinate, ethylsuccinate, citrate, acetate, lactate, methanesulfonate, benzoate, ascorbate, para-toluensulfonate, palmoate, salicylate, stearate, estolate, gluceptate or lactobionate salts, for example. At the same time, corresponding salts may contain pharmaceutically acceptable cations such as sodium, potassium, calcium, aluminum, ammonium, for example.

However, it is shown by the present invention, that the salt might reduce the solubility of pimobendan in the presence of fix amount of HPβCD. There are two ways to overcome this problem. The first option is to further increase the concentration of HPβCD. The other way is to keep restrict the amount of salts. It was shown, that after addition of phosphates resulting in an osmolality of about 300 mOsm/Kg the solubility of pimobendan in an exemplarily manner was not affected. Thus, according to a further aspect, the present invention relates to any of the above mentioned liquid preparations, preferably to aqueous solutions for injection, that comprise an etherified cyclodextrin derivative as described herein, preferably HPβCD, and a substituted benzimidazol as described herein, preferably pimobendan, wherein such liquid preparation contains an osmolality of about 250 to 350 mOsm/Kg, preferably of about 270 to 320 mOsm/Kg, even more preferably of about 280 to 300 mOsm/Kg. A person skilled in the art is able to adjust the osmolality of any of such liquid preparations to the above mentioned ranges by means well known in the art. For example, a liquid preparation that comprises about 24% (w/v) HPβCD and 0.75 mg/ml pimobendan may contain 10 mM of an alkali phosphate, preferably of sodium phosphate to adjust the osmolality of the final liquid preparation to about 290 to 300 mOsm/kg.

The pH of the liquid preparation according to the invention is preferably between 5.5 and 8.5. In particular, in case of an injectable solution, the pH is preferably between 6.5 and 7.5. Preferred buffer systems that can be used to adjust the pH to 6.5 to 7.5 are, for example, phosphate, acetate and citrate buffer systems. Preparations of any of those buffer systems are described for example in the European Pharmacopoeia (5$^{th}$ Edition 2005, European Directorate for the Quality of Medicines (EDQM), European Pharmacopoeia, 226 avenue de Colmar, F-67029 Strasbourg, France, http://www.pheur.org). Thus, according to a further aspect, the present invention relates to any of the above mentioned liquid preparations, preferably to aqueous solutions for injection, that comprise an etherified cyclodextrin derivative as described herein, preferably HPβCD, and a substituted benzimidazol as described herein, preferably pimobendan, wherein such liquid preparation is adjusted to pH 5.5 to 8.5, preferably to pH 6.5 to 7.5 in case of an injectable solution.

As described above, a preferred embodiment of the present invention relates to an injectable solution adjusted to pH 6 to 7.5, that comprise an etherified cyclodextrin derivative as described herein, preferably HPβCD, and a substituted benzimidazol as described herein, preferably pimobendan. In such case, the preparation of an isotonic solution would further be preferred.

In order to achieve an immediate onset of action of the substituted benzimidazol, preferably of pimobendan for all suitable indications, an injectable solution for parenteral administration by the i.v. and/or s.c. route is obligatory. An aqueous formulation is required to administer a drug product by the i.v./s.c. route to either humans or animals, formulations with a non-aqueous solvent are neither acceptable nor state of the art due to the risk of severe tolerance problems.

Thus according to a further aspect, the current invention relates to an injectable solution, i.e. for parenteral administration by the i.v. and/or s.c. route, comprising any of the liquid preparation as described above. It might be useful to administer the drug continuously over a defined period of time and not in a one-shot application. In such case, administration of an aqueous solution comprising the substituted benzimidazol, preferably pimobendan by infusion is advantageous. Thus according to a further aspect, the current invention relates to an injectable solution for infusion, comprising any of the liquid preparation as described above.

A solution is absolutely necessary for i.v. administration, suspended particles bear a high risk of emboli and have to be excluded. Ready-to-use solutions are preferred compared to lyophilised products which have to be reconstituted by adding a diluent/solvent before administration. The reconstitution of a drug product to be administered will add several minutes to the treatment which has to be avoided in a life-threatening situation as this. In addition local tolerance will depend on the isotonicity and pH range of the formulation. A pH in the neutral range of about pH 7 is usually preferred, the higher the actual pH deviates from this target the more likely the risk of not acceptable local tolerance.

Thus, according to a further aspect, the invention relates to any of the liquid preparations described herein and comprising an etherified cyclodextrin derivative as described herein, preferably HPβCD and a substituted benzimidazol as described herein, preferably pimobendan, wherein the liquid solution is a Ready-to use solution. The Ready-to-use solution is in general adjusted to a pH of about 6.5 to 7.5, preferably of about 6.8 to 7.2, even more preferred of about 7.0. Moreover, that Ready-to-use solution is also adjusted to an osmolality of about 250 to 350 mOsm/Kg, preferably of about 270 to 320 mOsm/Kg, even more preferably of about 280 to 300 mOsm/Kg. It was surprisingly found, that the addition of some salts resulting in about 300 mOsm/Kg significantly reduce the solubility of the substituted benzimidazol, in particular of pimobendan. However, it is in the knowledge of a person skilled in the art to slightly increase the osmolality of that Read-to-use solution to about 300 mOsm/Kg, e.g. to about 305 to 310 mOsm/Kg, that an appropriate solubility of the substituted benzimidazol, in particular of pimobendan is ensured.

According to a further aspect, the present invention relates to a liquid preparation as described supra, wherein the preparation comprises about i) 20 to 30% (w/w) of a HPβCD; ii) 0.005 to 0.15% (w/w) pimobendan, a pharmaceutical acceptable salt, derivative, metabolite or pro-drug thereof; and optional iii) 0.025 to 0.075% (w/w) of stabilizer preferably EDTA; and wherein the pH of the liquid preparation is adjusted to about 6.5 to 7.5 and the osmolality is about 280 to 300 mOsm/Kg.

According to a further aspect, the present invention also relates to a manufacturing process for the production of any of the liquid preparation as described herein. In the knowledge of the specific formulation of any of the above described liquid formulation, those formulations can be prepared according to stand procedures known to a person skilled in the art. That process comprises the steps:
a) Dissolving the etherified cyclodextrin derivative in a solvent;
b) Adding the substituted benzimidazol to the solution obtained in step (a); and
c) Admixing the mixture obtained in step (b) to obtain the liquid preparation in the form of an aqueous solution.

Preferably, that etherified cyclodextrin derivative is HPβCD. Moreover, the solvent preferably is water for injection.

According to more preferred embodiment that manufacturing process comprises the steps:
a) Weight the etherified cyclodextrin, preferably HPβCD into the manufacturing container;
b) Add water to approximately 40 to 80% of the final volume;
c) Mix until the etherified cyclodextrin dissolves using magnetic stirred or paddle stirrer;
d) Add any buffer component(s), transfer with water and mix until dissolved;
e) Check pH to ensure that it is close to the set-point. Adjust with sodium hydroxide or hydrochloric acid if required;
f) Add the substituted benzimidazol, preferably pimobendan, transfer with water and mix until dissolved;
g) Make to volume with water;

According to a even more preferred aspect, the manufacturing process comprises the steps:
h) Filter the liquid preparation of step g) and dispense into vials;
i) Autoclave the vials, preferably for 30 min at 121° C.

According to a further aspect, the present invention relates to the use of any of the liquid preparation as described herein as a medicament. Preferably that medicament is a veterinary medicament. Even more preferred, that medicament is a solution for injection. That solution for injection is, according to a further aspect an infusion solution.

As described supra, there is an unmet need in the field of medicine regarding the treatment of acute congestive heart failure (acute CHF) in animals and humans, and especially in dogs. Thus, the liquid preparation as provided herewith can be used in human and veterinary medicine, preferably in veterinary medicine. No product is licensed in veterinary medicine for this indication so far. So the treatment of acute CHF in a life-threatening situation would be an important innovation allowing to save the animal's life in an acute crisis situation. Due to an immediate onset of action, the rapid visual change of the animal's status would allow both the veterinarian and the animal owner to evaluate the success of the measures taken to overcome the situation. Additionally, this way of treatment would be a therapy option in cases where oral treatment is not possible. Perioperative administration to maintain cardiovascular function and/or renal perfusion during anaesthesia as well as treatment of shock and/or gastric dilation volvulus situations are other potential indications for a pimobendan formulation with an immediate onset.

Thus, according to a further embodiment, the present invention also relates the use of any of the liquid preparation comprising pimobendan described herein for preparing a pharmaceutical composition for the treatment or prevention of diseases in a subject in need of such treatment, selected from among the indications: congestive heart failure (CHF), acute CHF, decompensated endocardiosis (DCE), dilated cardiomyopathy (DCM), asymptomatic (occult) CHF, asymptomatic DCM, maintenance of cardiovascular function and/or renal perfusion during anaesthesia, shock, gastric dilation, volvulus, myocardial and renal ischemia. As described supra, the general therapeutically effective amount of pimobendan is about 0.05 to 0.5 mg pimobendan per kg body weight of the animal and application, preferably about 0.1 to 0.3 mg pimobendan per kg body weight of the animal and application, even more preferably about 0.15 mg pimobendan per kg body weight of the animal. Preferably, one dose is to be administered per day.

According to a further aspect, the present invention also relates to method of treatment and/or prevention of diseases, wherein cardiotonic, hypotensive, anti-inflammatory and anti-thrombotic substances have a therapeutic benefit comprising the step: administering to such subject in need of such treatment a therapeutically effective amount of any of the liquid preparations as described herein. Preferably, the liquid preparation is administered to a therapeutically effective amount of about 0.05 to 0.5 mg pimobendan per kg body weight of the animal and application, preferably about 0.1 to 0.3 mg pimobendan per kg body weight of the animal and application, even more preferably about 0.15 mg pimobendan per kg body weight of the animal. Preferably, one dose is to be administered per day.

As mentioned above, pimobendan is a well established medicament in the treatment of congestive heart failure (CHF), decompensated endocardiosis (DCE), dilated cardiomyopathy (DCM), asymptomatic (occult) CHF, asymptomatic DCM, among others. Thus according to a further aspect, the present invention directly relates to a method of treatment and/or prevention a subject suffering on or having a congestive heart failure (CHF), decompensated endocardiosis (DCE), dilated cardiomyopathy (DCM), asymptomatic (occult) CHF, asymptomatic DCM, myocardial and renal ischemia, shock, comprising the step: administering to said subject in need thereof any of the liquid preparations described herein and comprising a therapeutically effective amount of pimobendan. In particular, the therapeutically effective amount for the treatment of CHF is about 0.05 to 0.5 mg pimobendan per kg body weight of the animal and application, preferably about 0.1 to 0.3 mg pimobendan per kg body weight of the animal and application, even more preferably about 0.15 mg pimobendan per kg body weight of the animal and application. Preferably, one dose is to be administered per day. Such a treatment is also advantageous in the case of maintenance of cardiovascular function and/or renal perfusion during anaesthesia, shock, gastric dilation or volvulus, for examples caused by surgery, especially gastrointestinal surgery as well as trauma.

The subject in need of any such treatment mentioned above is a mammal, preferably a human or an animal. The term animal as used herein includes but is not limited to companion animals such as dogs, cats, guinea pigs, hamsters, horses, cattle, goats, sheeps or the like. Preferably, the subject in need of such treatment is a dog, horse or cat, most preferably a dog. However, such animal in need of such treatment also includes zoo animals such as monkies, elephants, giraffes and other ungulates, bears, mice and other small mammals.

The present invention furthermore relates to a kit of parts, that comprises
a) a container with a liquid preparation, preferably an injectable solution, according to the present invention as described herein,
b) and a package leaflet including the information that the liquid preparation, preferably the injectable solution, according to the present invention is to be used, preferably via injection (s.c. or i.v.), for the prevention and/or treatment of congestive heart failure in a subject in need of such prevention or treatment, preferably in a mammal as defined above.

In case of the treatment of an animal, that package leaflet preferably includes the information that the pimobendan is to be used at a dose as described supra, preferably of about 0.15 mg per kg body weight and application. Preferably, one dose is to be administered per day. More preferably, the package-leaflet includes the specific indication as described above.

According to a further aspect, the container comprises 2 ml, 5 ml, 10 ml, 50 ml, or 250 ml of the liquid preparation. Preferably the container comprises 3.75, 7.5 or 37.5 mg pimobendan.

EXAMPLES

The following examples serve to further illustrate the present invention; but the same should not be construed as a limitation of the scope of the invention disclosed herein.

Example: 1

Solubility of Pimobendan in the Presence of Hydroxypropyl-Beta-Cyclodextrin (HPβCD) at Different pH Values The solubility of pimobendan, a substituted benzimidazol, was tested at various concentrations of hydroxypropyl-beta-cyclodextrin (HPβCD) and at pH 3, 5 and 7. Kleptose® HP (Roquette, France) was used as HPβCD of pharmaceutical grade. Saturated solubility of pimobendan was investigated at 10 to 40% (w/v) of HPβCD at pH 3, 5, and 7. The solutions were buffered with a sodium phosphate solution. The sample solutions were prepared using the following method:
a) Approximately 3 ml of the solution under test was placed in a 7 ml glass vial with a magnetic stirring bar.
b) The pH was adjusted with hydrochloric acid
c) An excess of pimobendan was added. The sample was placed in an ultrasonic bath and sonicated for 5 min. to ensure an excess of pimobendan was present and more added if required;
d) The samples were placed in a water bath at 25° C. and stirred for at least 16 hours.
e) The samples were filtered using 0.2 μm PVDF syringe filter.
f) The samples were assayed by HPLC.

Figure 2:
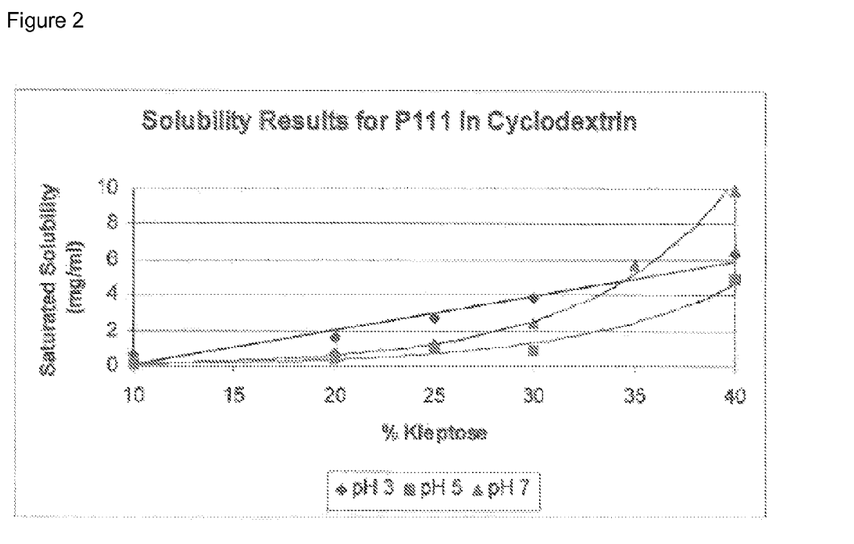

The results are shown in FIGS. 1 and 2. It was surprisingly found that due to a non-linear relationship between the rise in concentration of HPβCD and the increase in solubility of pimobendan both at a pH of about 5 or 7, solutions containing the target concentration for pimobendan could be obtained by the use of (HPβCD) concentration of more than 15% (see FIG. 1). In addition, it was an unexpected observation that the solubility enhancement achieved by HPβCD did not increase with decreasing pH, but that at pH 7 the solubility at a certain HPβCD concentration was lower at pH 7 than at pH 3, but higher than at pH 5. The relationship between increase of HPβCD concentration (by mass) and increase in saturated solubility of pimobendan was linear at pH 3, but non-linear at pH 5 and pH 7 (see FIG. 2).

Example: 2

Formulation Development

Figure 3:
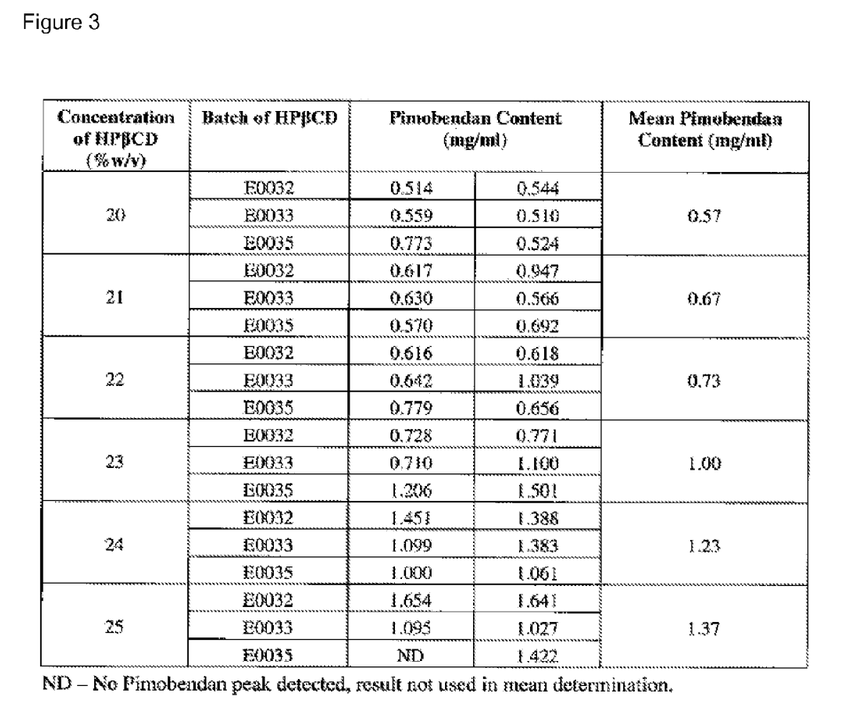
FIG. 3 shows the saturated solubility of pimobendan, a substituted benzimidazol in an aqueous solution comprising various 20 to 25% (w/v) of the etherified cyclodextrin-derivative hydroxypropyl-beta-cyclodextrin (HPβCD) dissolved in 10 mM phosphate buffer at pH 7.

1. Level of Hydroxypropyl-Beta-Cyclodextrin (HPβCD)
Saturated solubility of pimobendan was investigated at 20 to 25% (w/v) of HPβCD in 10 mM phosphate buffer pH 7.0. The study was carried out on three different batches of HPβCD and each solution tested in duplicate (see FIG. 3). The solutions were prepared using the following method:
a) Approximately 3 ml of the solution under test was placed in a 7 ml glass vial with a magnetic stirring bar.
b) An excess of pimobendan was added. The sample was placed in an ultrasonic bath and sonicated for 5 min. to ensure an excess of pimobendan was present and more added if required.
c) The samples were placed in a water bath at 25° C. and stirred for at least 16 hours.
d) The samples were filtered using 0.2 μm PVDF syringe filter.
e) The samples were assayed by HPLC.

A level of 22 to 24% (w/v) HPβCD was chosen for the formulations comprising 0.5, 0.75 and 1.0 mg/ml pimobendan.

Figure 4:
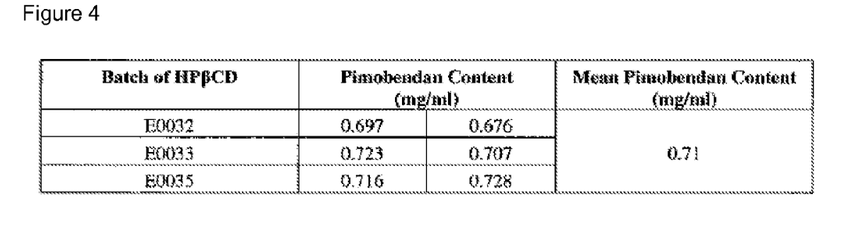
FIG. 4 shows the saturated solubility of pimobendan, a substituted benzimidazol in an aqueous solution comprising 24% (w/v) of the etherified cyclodextrin-derivative hydroxypropyl-beta-cyclodextrin (HPβCD) dissolved in 10 mM phosphate buffer and sodium chloride at pH 7.

2. Osmolality:
An isotonic solution was required for the formulation. The formulation with 24% (w/v) HPβCD and 10 mM phosphate buffer had an osmolality of 287 mOsm/Kg. Sodium chloride was added to increase the osmolality to 303 mOsm/Kg. Saturated solubility of pimobendan 0.75 mg/ml at 24% (w/v) HPβCD were investigated and results were compared with those formulations that were not supplemented with sodium chloride. Results are shown in FIG. 4. The amount of soluble pimobendan dramatically decreases from about 1.23 mg/ml to about 0.71 mg/ml.

3. Physical Stability:

A sample of the final formulation comprising 24% (w/v) HPβCD, 0.75 mg/ml pimobendan, 10 mM phosphate buffer, pH 7.0 was filtered through a 0.2 µm syringe PVDF filter into two screw cap class vials. One vial was stored at room temperature and the other at 5° C. Samples were assessed initially, after one and after two weeks for changes in appearance and sign of precipitation. No changes in appearance and no sign of precipitation were observed.

3. Filter Studies and Autoclaving Studies:

A) A sample of the final formulation comprising 24% (w/v) HPβCD, 0.75 mg/ml pimobendan, 10 mM phosphate buffer, pH 7.0 was filtered through three different filters (Fluorodyne® 0.2 µm (Pall); Durapore®, 0.22 µm (Millipore) and Supor® 0.2 µm (Pall)). For each experiment, 30 ml of the test solution was placed in a 50 ml syringe and then forced through an in-line holder housing a 47 mm membrane of each type. Filtrate samples were collected at sampling points 1, 2, 3, 4, 5, 10, 15 and 25 ml and analyzed to its pimobendan content. No change in the pimobendan content was measured for each filter system.

Figure 5:
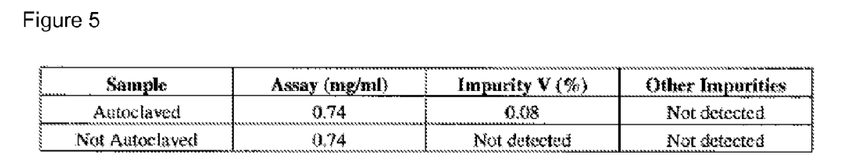
FIG. 5 shows the effect of autoclaving on the soluble formulation of pimobendan, a substituted benzimidazol.

B) A sample of the final formulation comprising 24% (w/v) HPβCD, 0.75 mg/ml pimobendan, 10 mM phosphate buffer, pH 7.0 was filtered through a 0.2 µm syringe PVDF filter and the filtrate was autoclaved at 121° C. for 30 min. The results are shown in FIG. 5. Only a small amount of degradation was observed when the formulation was autoclaved. The level was very low and indicates that the formulation can be autoclaved.

Example: 3

Manufacturing Process

The manufacturing process for the preparation of final formulation comprising HPβCD and pimobendan, is:
a) Weight the HPβCD into the manufacturing container;
b) Add water to approximately 60% of the final volume;
c) Mix until HPβCD dissolves using magnetic stirred or paddle stirrer;
d) Add the buffer components, transfer with water and mix until dissolved;
e) Check pH to ensure that it is close to pH 7.0. Adjust with sodium hydroxide or hydrochloric acid if required;
f) Add pimobendan, transfer with water and mix until dissolved;
g) Make to volume with water;
h) Filter the solution and dispense into vials;
i) Autoclave the vials for 30 min at 121° C.

Example: 4

| Liquid preparations | | |
|---|---|---|
| | mg/10 ml | |
| Material | Formulation # 1 | Formulation # 2 |
| A) | | |
| Pimobendan | 10 | 7.5 |
| Kleptose HP (HPβCD) | 3000.0 | 3000.0 |
| Citric acid monohydrate | 200.0 | 200.0 |
| NaOH 0.1N | q.s. ad pH 6.0 | q.s. ad pH 6.0 |
| Disodium edetate | 5.0 | 5.0 |
| Water for injection | q.s. to 10 ml | q.s. to 10 ml |
| B) | | |
| Pimobendan | 10 | 7.5 |
| Kleptose HP (HPβCD) | 2600.0 | 2400.0 |
| Disodium hydrogen phosphate dodecahydrate | 0.1343 | 0.1343 |
| Sodium dihydrogen phosphate dihydrate | 0.0975 | 0.0975 |
| Water for injection | q.s. to 10 ml | q.s. to 10 ml |
| c) | | |
| Pimobendan | 10 | 7.5 |
| Kleptose HP (HPβCD) | 2600.0 | 2400.0 |
| Disodium hydrogen phosphate dodecahydrate | 0.1343 | 0.1343 |
| Sodium dihydrogen phosphate dihydrate | 0.0975 | 0.0975 |
| Disodium edetate | 5.0 | 5.0 |
| Water for injection | q.s. to 10 ml | q.s. to 10 ml |
| D) | | |
| Pimobendan | 10.0 | 7.5 |
| Kleptose HP (HPβCD) | 3300.0 | 3000.0 |
| Disodium hydrogen phosphate dodecahydrate | 17.6 | 17.6 |
| Sodium dihydrogen phosphate dihydrate | 8.0 | 8.0 |
| Methyl paraben | 20.0 | 10.0 |
| Propyl paraben | 5.0 | 5.0 |
| Disodium edetate | 5.0 | 5.0 |
| Water for injection | q.s. to 10 ml | q.s. to 10 ml |
| E) | | |
| Pimobendan | 10 | 7.5 |
| Kleptose HP (HPβCD) | 2500.0 | 2300.0 |
| Disodium hydrogen phosphate dodecahydrate | 17.6 | 17.6 |
| Sodium dihydrogen phosphate dehydrate | 8.0 | 8.0 |
| Disodium edetate | 5.0 | 5.0 |
| Water for injection | q.s. to 10 ml | q.s. to 10 ml |

The invention claimed is:

1. A liquid preparation comprising an etherified cyclodextrin derivative and pimobendan or a pharmaceutically acceptable salt thereof, wherein the etherified cyclodextrin derivative is selected from the group consisting of alpha-, beta, and gamma-cyclodextrin ether, and wherein the liquid preparation has a pH of 5.5 to 8.5.

2. The liquid preparation according to claim 1, wherein the etherified cyclodextrin derivative is hydroxypropyl-beta-cyclodextrin.

3. The liquid preparation according to claim 1, wherein the portion of the etherified cyclodextrin derivative contains about 15 to 40% (w/v).

4. The liquid preparation according to claim 3, wherein the portion of the etherified cyclodextrin derivative contains about 20 to 30% (w/v).

5. The liquid preparation according to claim 1, wherein the portion of pimobendan or a pharmaceutical salt thereof contains about 0.005 to 0.15% (w/v).

6. The liquid preparation according to claim 1, wherein the preparation has pH value of about 6.5 to 7.5 and an osmolality of about 280 to 300 mOsm/Kg.

7. The liquid preparation according to claim 1, wherein the preparation comprises about:
  a) 20 to 30% (w/v) of a hydroxypropyl-beta-cyclodextrin;
  b) 0.005 to 0.15% (w/v) pimobendan or a pharmaceutical acceptable salt thereof;

and wherein the pH of the liquid is adjusted to about 6.5 to 7.5 and the osmolality is about 280 to 300 mOsm/Kg.

8. The liquid preparation according to claim 1, wherein the preparation further comprises pharmaceutical acceptable carriers, excipients, and/or salts.

9. The liquid preparation according to claim 1, wherein the preparation is isotonic.

10. The liquid preparation according to claim 1, wherein the preparation contains one or more suitable preservatives.

11. The liquid preparation according to claim 1, wherein the liquid preparation further comprises 0.025 to 0.075% (w/v) of one or more stabilizers.

12. A kit of parts that comprises:
a) a liquid preparation according to claim 1; and
b) a package leaflet including information that the liquid preparation is to be used for the prevention and/or treatment of congestive heart failure in a subject in need of such prevention or treatment.

\* \* \* \* \*